United States Patent
Bearnson et al.

(10) Patent No.: US 6,394,769 B1
(45) Date of Patent: May 28, 2002

(54) PUMP HAVING A MAGNETICALLY SUSPENDED ROTOR WITH ONE ACTIVE CONTROL AXIS

(75) Inventors: Gill B. Bearnson; Pratap S. Khanwilkar, both of Salt Lake City; James W. Long, Holladay; Jed C. Ludlow, North Salt Lake, all of UT (US); Brad E. Paden; Chen Chen, both of Santa Barbara, CA (US); Dave B. Paden, Goleta, CA (US); Don B. Olsen, Salt Lake City, UT (US); James Antaki, Allison Park, PA (US); Paul E. Allaire; Michael Baloh, both of Charlottesville, VA (US)

(73) Assignees: Medquest Products, Inc., Salt Lake City, UT (US); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/602,471

(22) Filed: Jun. 23, 2000

Related U.S. Application Data

(63) Continuation-in-part of application No. 09/459,146, filed on Dec. 10, 1999, which is a continuation-in-part of application No. 08/850,156, filed on May 2, 1997, now abandoned.

(60) Provisional application No. 60/168,102, filed on Nov. 30, 1999, and provisional application No. 60/016,857, filed on May 3, 1996.

(51) Int. Cl.$^7$ ................................................. F04B 17/00
(52) U.S. Cl. ............................ 417/423.7; 417/423.12; 417/356; 415/900
(58) Field of Search .................... 417/423.7, 423.12; 415/900, 58.2, 58.3, 58.4, 57.3, 57.4

(56) References Cited

U.S. PATENT DOCUMENTS

| | | | |
|---|---|---|---|
| 3,860,300 A | 1/1975 | Lyman | 308/10 |
| 4,683,391 A | 7/1987 | Higuchi | 310/30.5 |
| 4,688,998 A | 8/1987 | Olsen et al. | 417/356 |
| 5,044,897 A | 9/1991 | Dorman | 417/423.7 |
| 5,055,005 A | * 10/1991 | Kletschka | 417/356 |
| 5,112,202 A | 5/1992 | Oshima et al. | 417/423 |
| 5,195,877 A | 3/1993 | Kletschka | 417/356 |
| 5,302,874 A | 4/1994 | Pinkerton | 310/90.5 |
| 5,470,208 A | * 11/1995 | Kletschka | 417/356 |
| 5,576,587 A | 11/1996 | Takahashi et al. | 310/90.5 |
| 5,666,014 A | 9/1997 | Chen | 310/90.5 |
| 5,685,700 A | 11/1997 | Izraelev | 417/423.7 |
| 5,777,414 A | 7/1998 | Conrad | 310/90.5 |
| 5,783,885 A | 7/1998 | Post | 310/90.5 |
| 5,840,070 A | 11/1998 | WAmpler | 604/131 |
| 5,938,412 A | * 5/1999 | Izraelev | 417/423.7 |
| 6,015,275 A | 1/2000 | Suski et al. | 417/423.2 |
| 6,047,180 A | 6/2000 | Khanwilkar et al. | 417/356 |
| 6,074,180 A | * 6/2000 | Khanwilkar et al. | 417/356 |
| 6,244,835 B1 | * 6/2001 | Antaki et al. | 417/356 |

FOREIGN PATENT DOCUMENTS

WO     WO 99/53974     10/1999

* cited by examiner

*Primary Examiner*—Cheryl J. Tyler
(74) *Attorney, Agent, or Firm*—Madson & Metcalf

(57) ABSTRACT

An inventive blood pump in accordance with this invention includes a housing that has inlet and outlet ports for receiving and discharging blood. A rotor is positioned in the housing's interior for pumping blood between the housing's inlet and outlet ports, with the rotor being capable of motion in three translational and three rotational axes. An assembly for magnetically suspending and rotating the rotor in a contact-free manner with respect to the housing includes only one electromagnetic bearing that actively controls motion of the rotor with respect to one axis selected from the rotor's three translational and three rotational axes, an electromagnetic motor that actively drives motion of the rotor with respect to one of its three rotational axes, and magnetic bearings for passively controlling motion of the rotor with respect to the remaining four of its translational and rotational axes. The inventive blood pump can also be incorporated into an artificial heart.

21 Claims, 15 Drawing Sheets

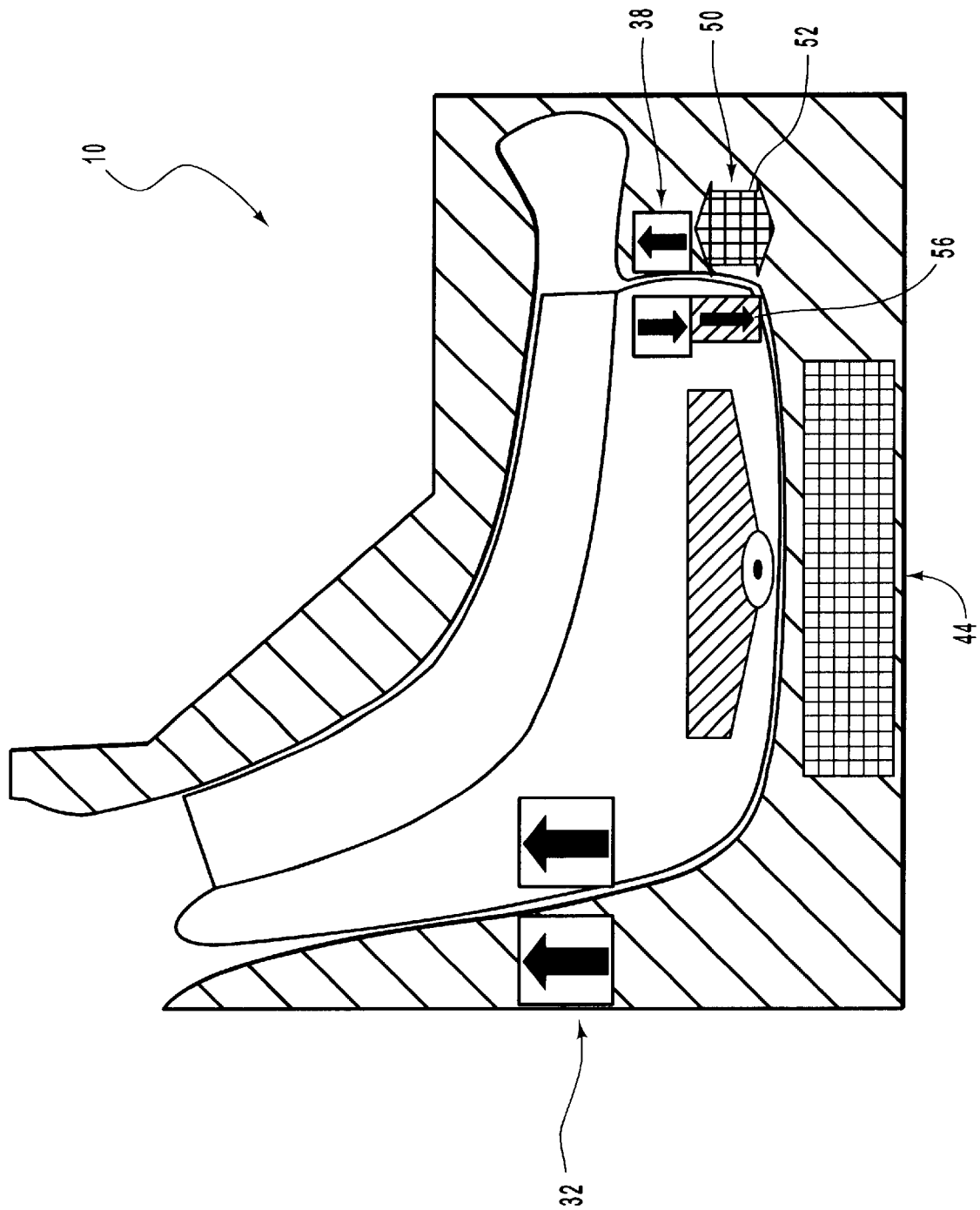

PUMP HAVING A MAGNETICALLY SUSPENDED ROTOR WITH ONE ACTIVE CONTROL AXIS

RELATED APPLICATIONS

This application claims priority from U.S. Provisional Patent Application No. 60/168,102, filed Nov. 30, 1999, entitled "Control Algorithms for Implantable Blood Pump Supported in Magnetic Bearing."

Also, this application is a continuation-in-part of pending U.S. patent application Ser. No. 09/459,146, filed Dec. 10, 1999, entitled "Electromagnetically Suspended and Rotated Centrifugal Pumping Apparatus and Method," which is a continuation-in-part of abandoned U.S. patent application Ser. No. 08/850,156, filed May 2, 1997, entitled "Electromagnetically Suspended and Rotated Centrifugal Pumping Apparatus and Method," which claimed priority from U.S. Provisional Patent Application No. 60/016,857, filed May 3, 1996, entitled "Electromagnetically Suspended and Rotated Centrifugal Pumping Apparatus and Method."

Further, this application claims priority from pending PCT Patent Application No. PCT/US99/08870, filed Apr. 22, 1999, entitled "Implantable Centrifugal Blood Pump With hybrid Magnetic Bearings," which claims priority from abandoned U.S. patent application Ser. No. 09/064,352, filed Apr. 22, 1998, entitled "Implantable Centrifugal Blood Pump With Hybrid Magnetic Bearings," which was a continuation-in-part of U.S. patent application Ser. No. 08/850,598, filed May 2, 1997, entitled "Hybrid Magnetically Suspended and Rotated Centrifugal Pumping Apparatus and Method," now U.S. Pat. No. 6,074,180, which claims priority from U.S. Provisional Patent Application No. 60,016,856, filed May 3, 1996, entitled "Hybrid Magnetically Suspended and Rotated Centrifugal Pumping Apparatus and Method."

TECHNICAL FIELD OF THE INVENTION

This invention relates to pumps having magnetically suspended rotors with three translational and three rotational axes of motion, one of which (translational or rotational) is actively controlled, another of which (rotational) is actively driven, and the remainder of which (translational and rotational) are passively controlled (meaning, for example, that no electronic controller is required). Such pumps are particularly suited to the task of pumping blood in humans and other animals.

BACKGROUND OF THE INVENTION

There are many types of fluid pumps suitable for use in a wide range of applications, all performing the same basic function of moving fluid from one point to another, or moving a fluid from one energy level to another. However, pumps for pumping sensitive fluids, such as blood, introduce special design requirements. Additionally, pumps for implantation in a human patient for long or short-term use as ventricular assist devices (VAD's) or complete heart replacement, add additional size, weight, durability, and other requirements.

The design problems associated with sensitive fluids, including blood, generally relate to problems caused by contact of the fluid with mechanical parts and other substances present in the pump. Problem contact areas for sensitive fluids may include contact with materials and structures in rotating fluid seals, contact with mechanical bearing assemblies that are exposed to the fluid, and use in bearing structures that depend on a layer of fluid between moving, surfaces to provide reduced friction, such as hydrodynamic bearings. For example, it is well known that rotating shaft seals are notoriously susceptible to wear, failure, and even attack by some fluids. Many types of pumps may also increase mechanical working of the fluid and precipitate detrimental processes such as chemical reactions or blood clotting.

It is also well known that pumps for corrosive fluids, blood, and fluids used in food processing require careful design of the flow passages to avoid fluid damage, contamination, and other undesirable conditions. For example, ball bearing and other rolling-element bearings must in general be used with some type of shaft seal to isolate the fluid from the bearing. This may be needed to prevent damage to the bearing by caustic fluids, or to prevent damage to the fluid by the rolling elements of the bearing. For example, rolling-element bearings can crush and destroy the living cells in blood. Thus, rolling-element bearings are generally not practical for blood pumps.

Moreover, high shear and stagnation should be avoided in blood pumps. It is well known that there are limits to the time that red blood cells can withstand high mechanical shear. Red blood cells are subject to damage or rupture (hemolysis) if these limits are exceeded. In the other extreme, blood is particularly susceptible to clotting in regions of stagnation and low flow.

Finally, the size, weight, biocompatibility, and operating durability and reliability of blood pumps are a major concern when such pumps are used as VAD's or heart replacement pumps. It would be desirable to have a VAD or heart replacement pump that can operate reliably for periods of time up to twenty or thirty years despite the normal bumping and jarring of everyday life, including unexpected impact such as from falling, yet is small enough to implant easily in a patient's chest. It is also desirable to reduce the power requirements of such a pump so as to minimize battery size and thus increase mobility of the patient.

To address these problems, pumps with magnetically suspended impellers have been developed. For example U.S. Pat. No. 5,112,202 to Oshima discloses a pump in which the impeller is magnetically suspended or levitated within the pump housing, and is magnetically, not mechanically, coupled to the pump housing. The pump employs permanent magnets rotating, on a motor external to the pumping chamber, with the external permanent magnets magnetically coupled to opposing permanent magnets on the impeller. Such magnetically suspended pumps are well adapted to pumping sensitive fluids because they eliminate the mechanical bearing structure or rotating seals which can damage, or be damaged by, the fluid.

However, such pumps also present several drawbacks. First, an external motor with its own means of bearing support (ball bearings) is still required to rotate the impeller. It is the external bearing support that maintains the position of the rotor in such a pump. Though the motor is sealed from contact with blood and other bodily fluids, and is magnetically coupled to the suspended impeller, it still employs bearings that produce heat and can be prone to failure. Naturally, such pumps tend to be bulky in part because of the size of the electric motor. These pumps are frequently unsuitable for implantation in a patient because of size, weight, power consumption, and durability problems.

Other methods of magnetically supporting a rotating pump impeller have been developed. For example, U.S. Pat. No. 4,688,998 to Olsen teaches a fully suspended pump rotor employing permanent magnet rings on the rotor magnetized along the axis of rotation, and actively controlled electromagnets on the stator that create a magnetic field to stabilize the position of the rotor. This approach also leaves certain problems unsolved. While the manufacture of permanent magnets has advanced substantially, there are still significant process variations. These variations include repeatability from one magnet to the next, and homogeneity of the material within one magnet. The position and stability of the rotor in the Olsen invention is entirely dependent on the homogeneity of the permanent magnet rings. These problems are well known by designers of electro-mechanical devices, where significant steps are normally taken to reduce the dependency of device performance on homogeneous magnets. In the field of permanent magnet motors, this is a well known source of torque ripple.

U.S. Pat. No. 5,443,503 to Yamane discloses an artificial heart pump that includes a cylindrical stator surrounding and magnetically suspending a rotor that contacts the pump's housing at a mechanical pivot point. The failure to provide a contactless rotor increases the heat generation and energy consumption of the rotor, thus making this pump less than desirable as a blood pump. In addition, the mechanical pivot point is a location of blood damage and stagnation that may lead to clotting.

There is thus an ongoing interest in providing a practical implantable blood pump with a magnetically suspended, contactless rotor for pumping human blood without damaging the blood. Such a pump should have reduced complexity, reduced cost, and improved reliability.

SUMMARY OF THE INVENTION

An inventive blood pump in accordance with this invention includes a housing that has inlet and outlet ports for receiving and discharging blood. A rotor is positioned in the housing's interior for pumping blood between the housing's inlet and outlet ports, with the rotor being capable of motion in three translational and three rotational axes. An assembly for magnetically suspending and rotating the rotor in a contact-free manner with respect to the housing includes only one electromagnetic bearing that actively controls motion of the rotor with respect to one axis selected from the rotor's three translational and three rotational axes, an electromagnetic motor that actively drives motion of the rotor with respect to one of its three rotational axes, and magnetic bearings for passively controlling motion of the rotor with respect to the remaining four of its translational and rotational axes. As used herein, the term "passively controlling" refers, for example, to a method of controlling motion of the rotor using magnetic fields that does not depend upon an electronic controller to modulate the fields. Also, the inventive blood pump can be incorporated into an artificial heart or ventricular assist device.

In another embodiment of this invention, blood is pumped through a human or other animal's body by immersing a pump rotor capable of motion in three translational and three rotational axes in the blood. The pump rotor is magnetically suspended in a contact-free manner with a plurality of passive magnetic bearings and only one active electromagnetic bearing structure, and the pump rotor is rotated with a magnetic motor. The magnetic suspension and rotation of the pump rotor is actively controlled with respect to only one of the pump rotor's three translational and three rotational axes using the electromagnetic bearing structure.

BRIEF DESCRIPTION OF THE FIGURES

FIGS. 4A and 4B are cross-sectional, partial views illustrating alternative versions of another embodiment of a magnetic suspension and rotation assembly for the blood pump of FIG. 1;

DETAILED DESCRIPTION OF THE ILLUSTRATED EMBODIMENTS

Figure 1:
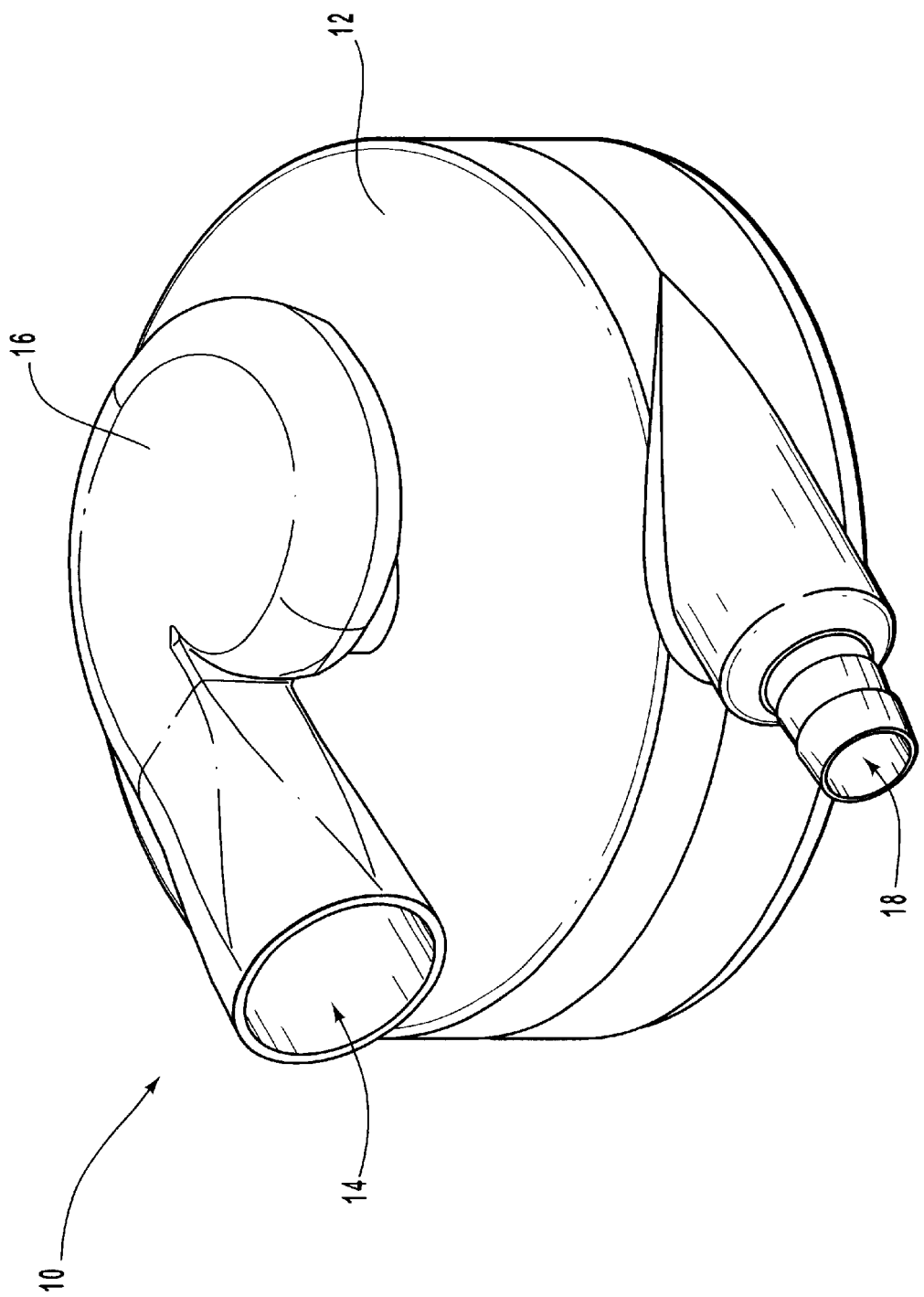
FIG. 1 is an isometric view of a blood pump in accordance with this invention.

As shown in FIG. 1, a blood pump 10 in accordance with this invention includes a housing 12 with an inlet 14, flow turning structure 16, and outlet 18. The flow turning structure 16 is configured to redirect incoming fluid flow through an acute angle in a gentle, low-thermal manner using a compact design. The structure 16 is configured such that flow swirls around in a logarithmic spiral configuration, equalizing the flow rate and pressure entering the inlet 14. Additionally, this spiral configuration reduces flow eddies and other disruptions in the flow that are detrimental to pump efficiency. The redirection of flow is thus accomplished in a gentle manner with low fluid stress that is consistent with use in a pump for sensitive fluids.

Figure 2:
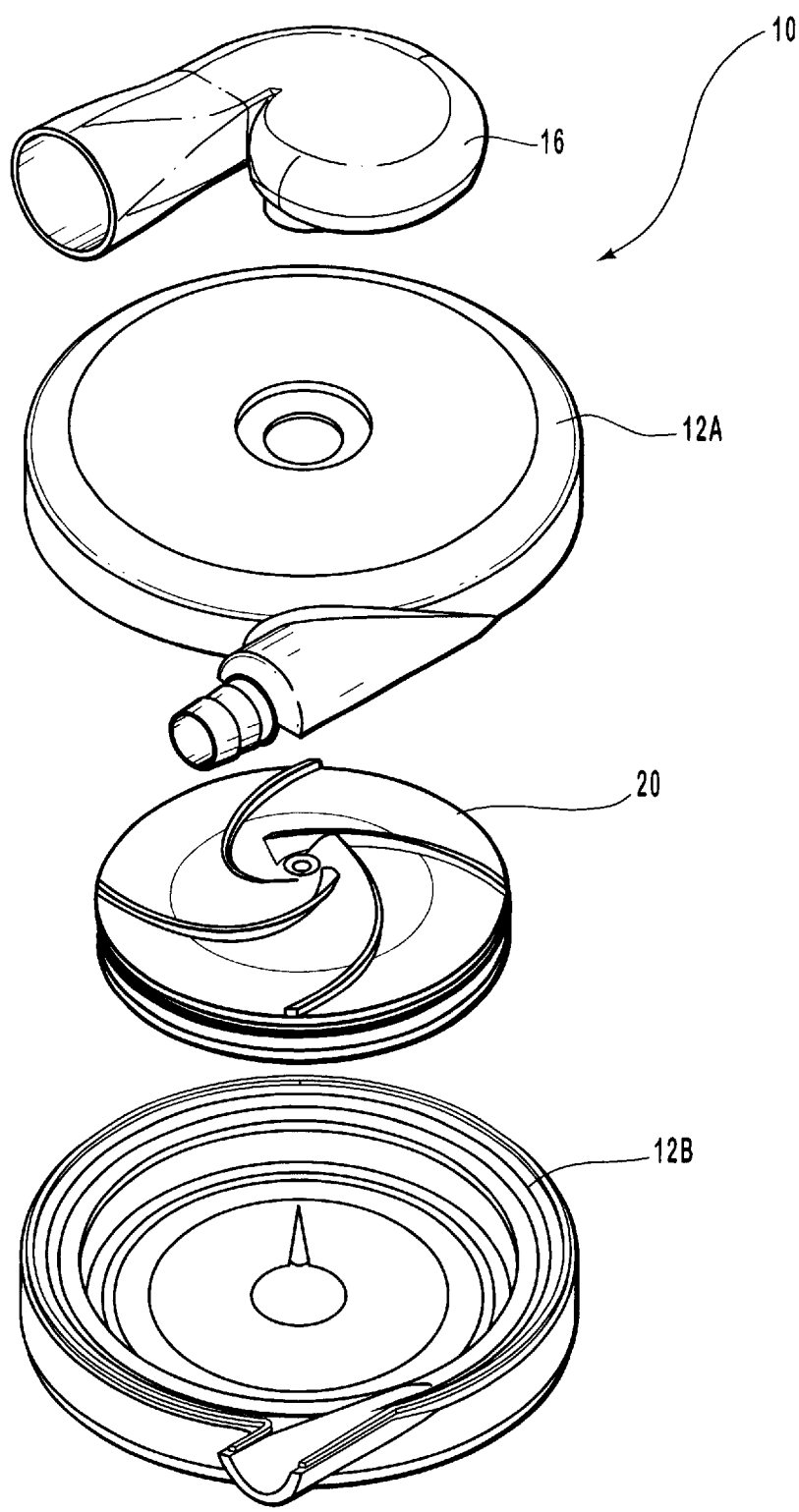
FIG. 2 is an exploded view of the blood pump of FIG. 1.

As shown in more detail in FIG. 2, the blood pump 10 of FIG. 1 includes the flow turning structure 16, upper and lower halves 12A and 12B of the housing 12, and an impeller assembly 20. The impeller assembly 20 is designed to function as the rotor of a motor, and includes soft iron magnetic material structures and permanent magnet structures that act as targets on the rotor for magnetic bearing actuators, as will be described in more detail below.

Figure 3A:
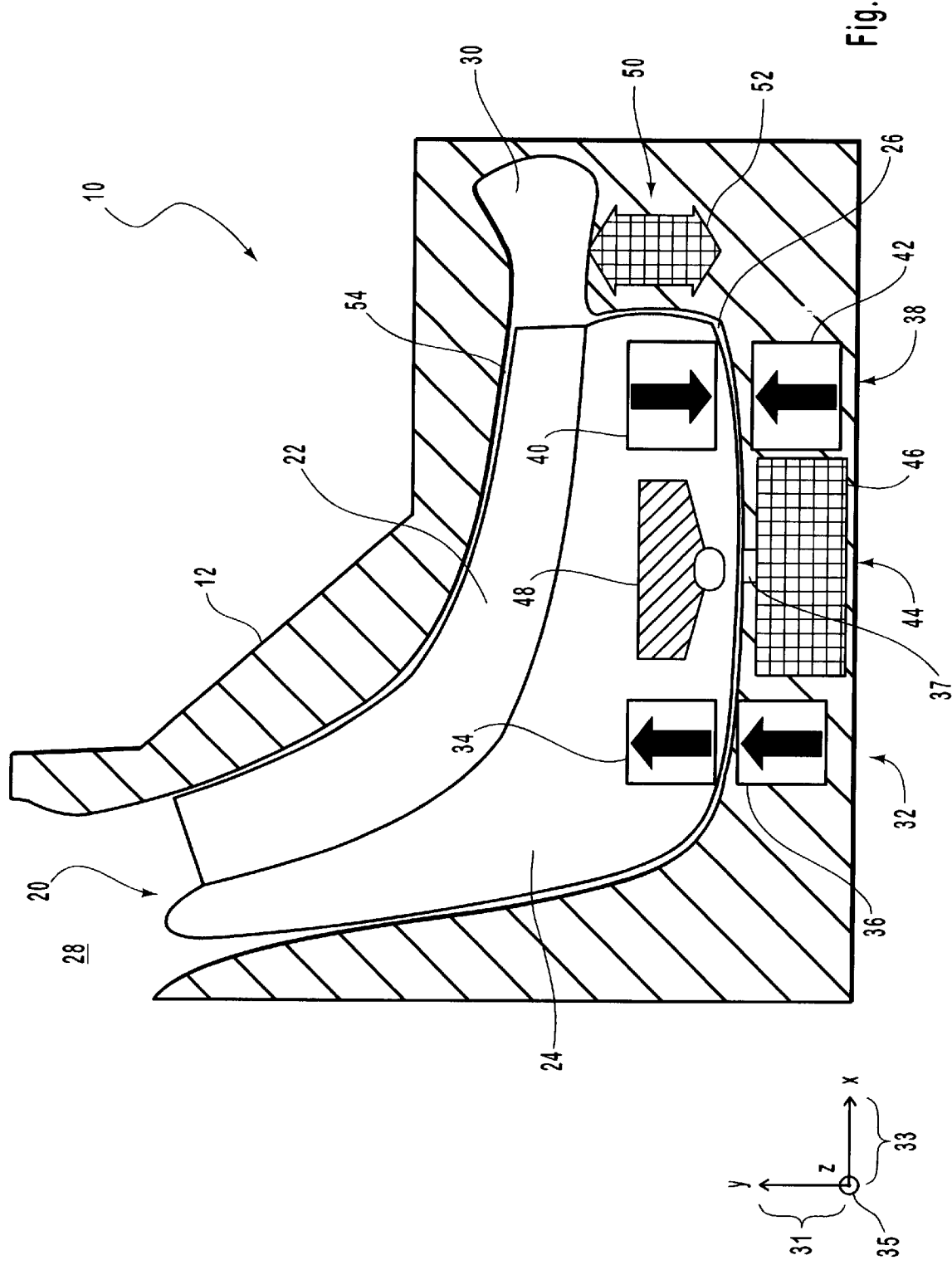
FIGS. 3A and 3B are cross-sectional, partial views illustrating alternative versions of one embodiment of a magnetic suspension and rotation assembly for the blood pump of FIG. 1.

As shown in more detail in a partial, cross-sectional view in FIG. 3A, the impeller assembly 20 includes a plurality of vanes 22 (only one shown) and a hub 24 that supports the vanes 22. The housing 12 is formed to provide curved or straight fluid gaps 26 around the rotating impeller assembly 20. The gaps 26 are configured to work in conjunction with the impeller assembly 20 to accommodate flow without damaging blood or other sensitive fluids. This is accomplished by making the flow passage gaps 26 short in length, yet with large bending radii to allow gentle backflow around the hub 24.

The vanes 22 of the impeller assembly 20 drive sensitive fluid (e.g., blood) from adjacent an inlet 28 into a pump volute 30, which is formed around the perimeter of the inner space of the housing 12. The volute 30 is formed in a logarithmic spiral shape, more evident in FIG. 2, which spirals about the center of the pump 10, gathering flow from the impeller vanes 22, and directing it to the tangentially aligned outlet 18 (see FIG. 1). This configuration minimizes damage to blood or other sensitive fluids by gradually redirecting the flow across the vanes 22 from the inflow 28 to the pump volute 30, where the flow is then directed to the outlet 18 (FIG. 1).

The blood pump 10 of FIG. 3A further includes a passive radial bearing 32 composed of a pair of permanent magnet structures 34 and 36, a passive moment bearing 38 composed of a pair of permanent magnet structures 40 and 42, an electromagnetic motor 44 composed of a motor winding 46 and motor permanent magnet 48, and an electromagnetic axial bearing 50 composed of an active thrust coil 52 and the permanent magnet 40. If the impeller assembly 20 is aligned with an x-axis 33 that extends from left to right across FIG. 3A, a y-axis 31 that extends from bottom to top across FIG. 3A, and a z-axis 35 that extends directly out of the page in FIG. 3A, then the passive radial bearing 32 largely controls translational movement of the impeller assembly 20 in the x-z plane, the passive moment bearing 38 largely controls rotational movement of the impeller assembly 20 about the x-axis 33 and the z-axis 35, the electromagnetic motor 44 drives rotational movement of the impeller assembly 20 about the y-axis 31, and the electromagnetic axial bearing 50 controls translational movement of the impeller assembly 20 along the y-axis 31. Control is achieved through the use of a gap sensor 37, as will be discussed in more detail below.

The passive radial bearing 32 produces an attractive force between its two races (i.e., the magnet structures 34 and 36) that is used to cancel a similar repulsive force between the races (i.e., the magnet structures 40 and 42) of the passive moment bearing 38 when the impeller assembly 20 is in a centered or neutral position. It is understood, of course, that any combination of structures can be used so long as such structures preferably provide an equilibrium position for the impeller assembly 20 and provide positive restoring forces to the assembly 20 when it is displaced along or about the x and/or z-axes 33 and 35.

The permanent magnet structures 34, 36, 40, and 42 may be either a single magnet ring or a stacked structure of several magnet rings. These magnet rings can be magnetized in either a radial or axial direction. In the case of a stacked structure, the magnetization of adjacent magnets may be in opposing but parallel directions, or in perpendicular directions. A gradually rotating magnetization direction can also be used. In addition, dimensions of the individual magnet rings involved in the structures may vary from one ring to another. All dimensions, along with air gap lengths, can be determined through a process of optimal design, which aims at achieving maximal bearing forces while minimizing certain dimensions or overall volume.

It should be noted that movement of the impeller assembly 20 in this embodiment is actively controlled in only one axis (in addition to the motor), namely, the y-axis 31 (in which translational movement is controlled by the electromagnetic axial bearing 50 working in combination with the moment bearing 38). This greatly simplifies the design, and reduces the overall cost, of the blood pump 10, thus making the pump 10 more practical to implement, in contrast to those blood pump designs that require multiple axes of active control. Of course, it will be understood by those having skill in the technical field of this invention that although the single actively controlled axis is shown in FIG. 3A as being y-axis translation motion, it may be any of the other five control axes instead. Simplification of the design of the blood pump 10 allows for the elimination of a top shroud that typically would cover the vanes 22, since such a shroud is no longer needed to support the presence of electromagnetic elements attached to the top of the impeller assembly 20. The elimination of such a shroud in turn reduces the possibility of blood clots being generated in a top gap 54 between the impeller assembly 20 and the housing 12.

It should also be noted that hydrodynamic principles can be applied either to the bottom surface of the hub 24, or to the portion of the housing 12 that faces the hub 24 across the gap 26, in order to generate extra "lift" for the impeller assembly 20 as it rotates. Such principles would lead to a variable gap dimension along the gap 26, or the inclusion of hydrodynamic bearings spaced circumferentially around the housing 12 or the impeller assembly 20 adjacent the gap 26.

Figure 3B:
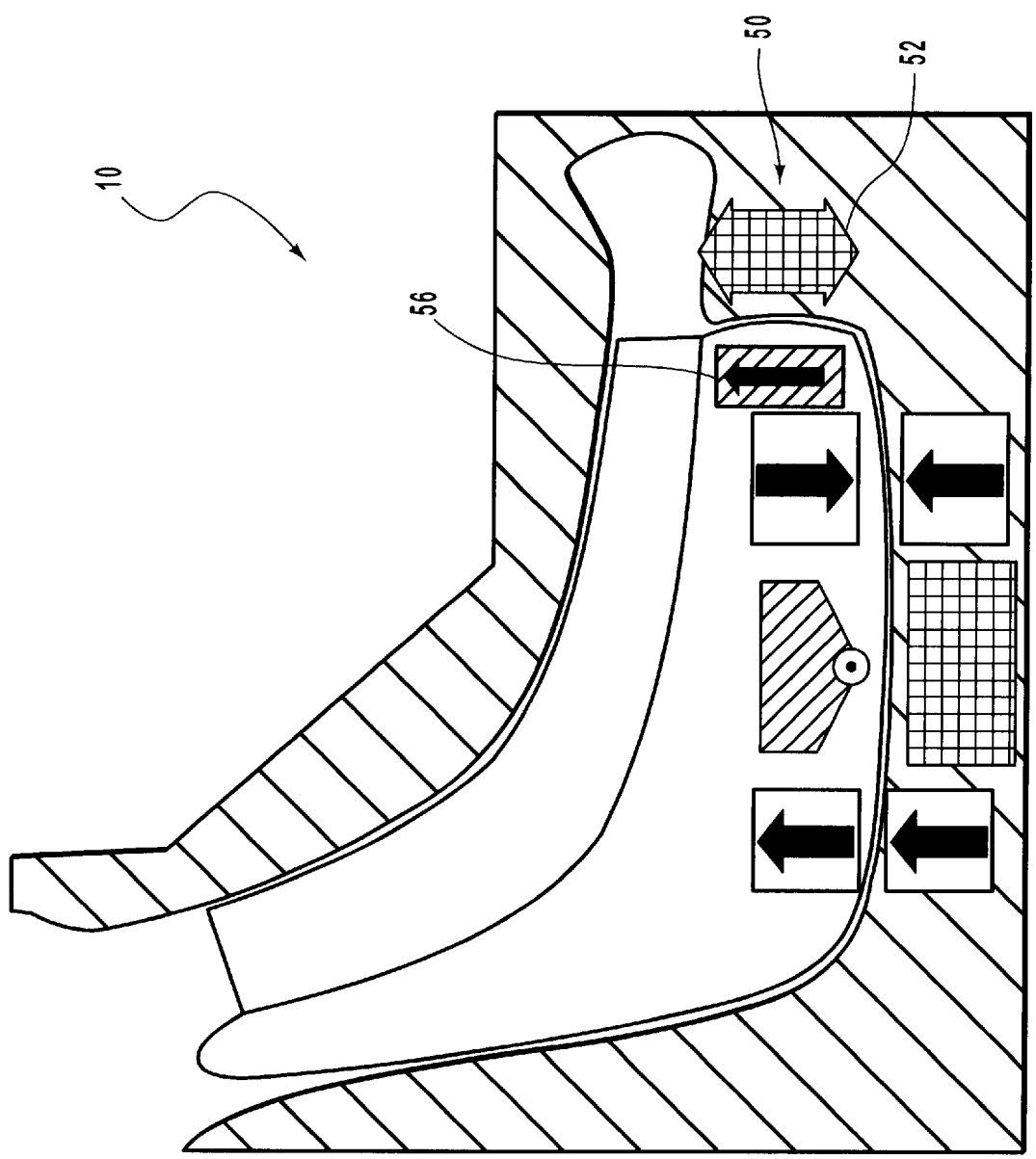

As shown in FIG. 3B, in an alternative version of the blood pump 10 of FIG. 3A, the electromagnetic axial bearing 50 includes an active thrust permanent magnet structure 56 in addition to the permanent magnet 40 of FIG. 3A. This permits the permanent magnet 40 of FIG. 3A to exclusively serve the moment bearing 38. The magnet structure 56 can be composed of a single magnet ring or stacked magnet rings with radial or axial magnetization, in a manner similar to the magnet structure in the passive bearings 32 and 38. The winding of the axial bearing 50, on the other hand, is composed of one or more coils, with directions of current chosen to maximize the efficiency of the bearing 50. Again, the sizes and locations of these coils can be determined through optimal design.

As shown in FIG. 4A, in another alternative version of the blood pump 10, the passive radial bearing 32 is repositioned toward the center of the pump 10, the passive moment bearing 38 is repositioned toward the edge of the pump 10, the electromagnetic motor 44 takes up most of the lower portion of the pump 10, and the electromagnetic radial bearing 50 consists of the active thrust coil 52 and the permanent magnet structure 56.

Figure 4B:
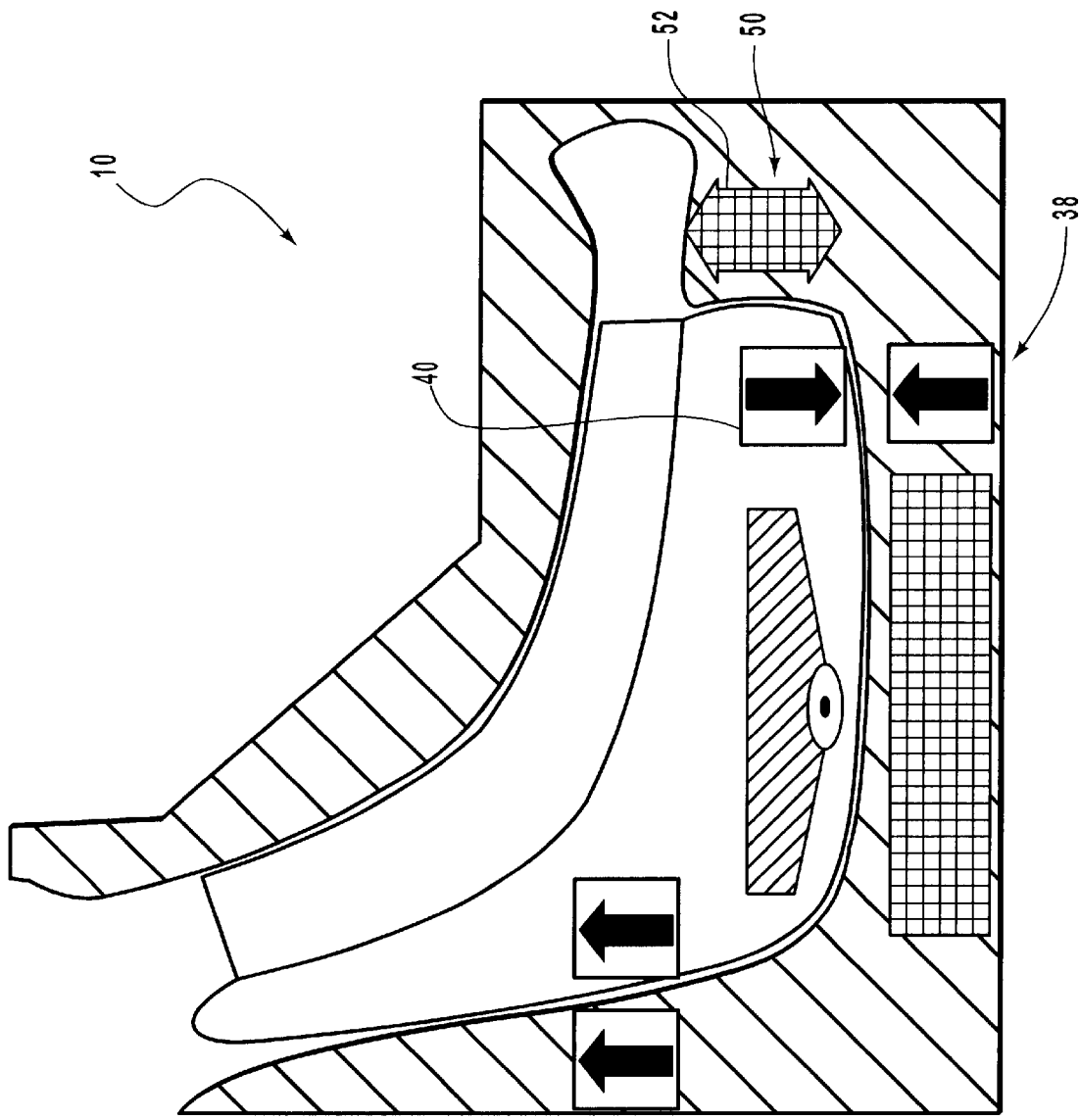

As shown in FIG. 4B, in another alternative version of the blood pump 10, the passive moment bearing 38 is repositioned toward the bottom of the pump 10, and the electromagnetic radial bearing 50 consists of the active thrust coil 52 and the permanent magnet structure 40, which serves the dual functions of moment bearing race and thrust bearing component.

Figure 5:
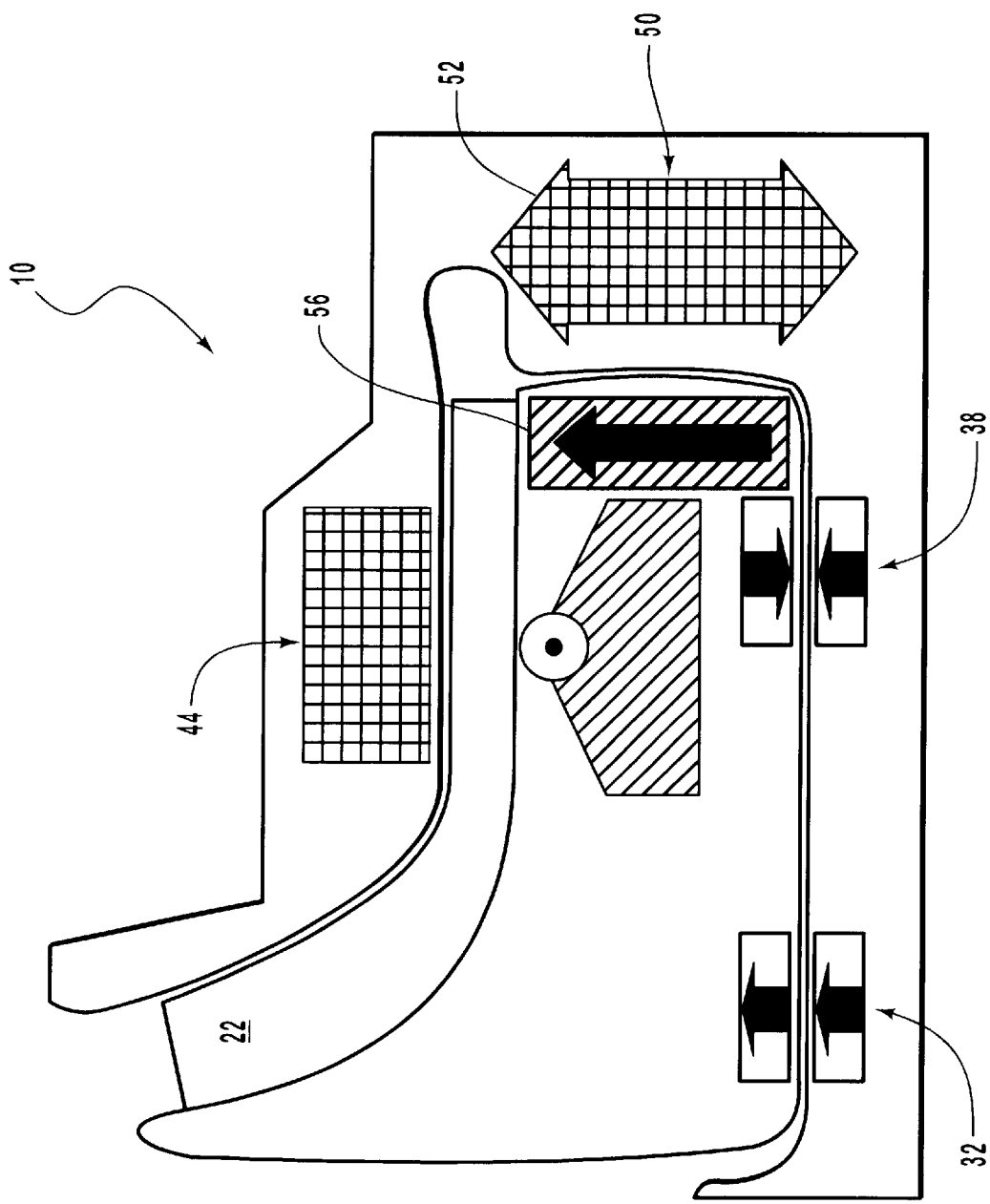
FIG. 5 is a cross-sectional, partial view illustrating still another embodiment of a magnetic suspension and rotation assembly for the blood pump of FIG. 1.

As shown in FIG. 5, in a more compact, alternative version of the blood pump 10, the passive radial bearing 32 is positioned along the bottom of the pump 10, the passive moment bearing 38 is positioned along the bottom of the pump 10, the electromagnetic motor 44 is repositioned along the top of the pump 10 with its gap spanning across the vanes 22, and the electromagnetic axial bearing 50 consists of the active thrust coil 52 and the permanent magnet structure 56.

Figure 6:
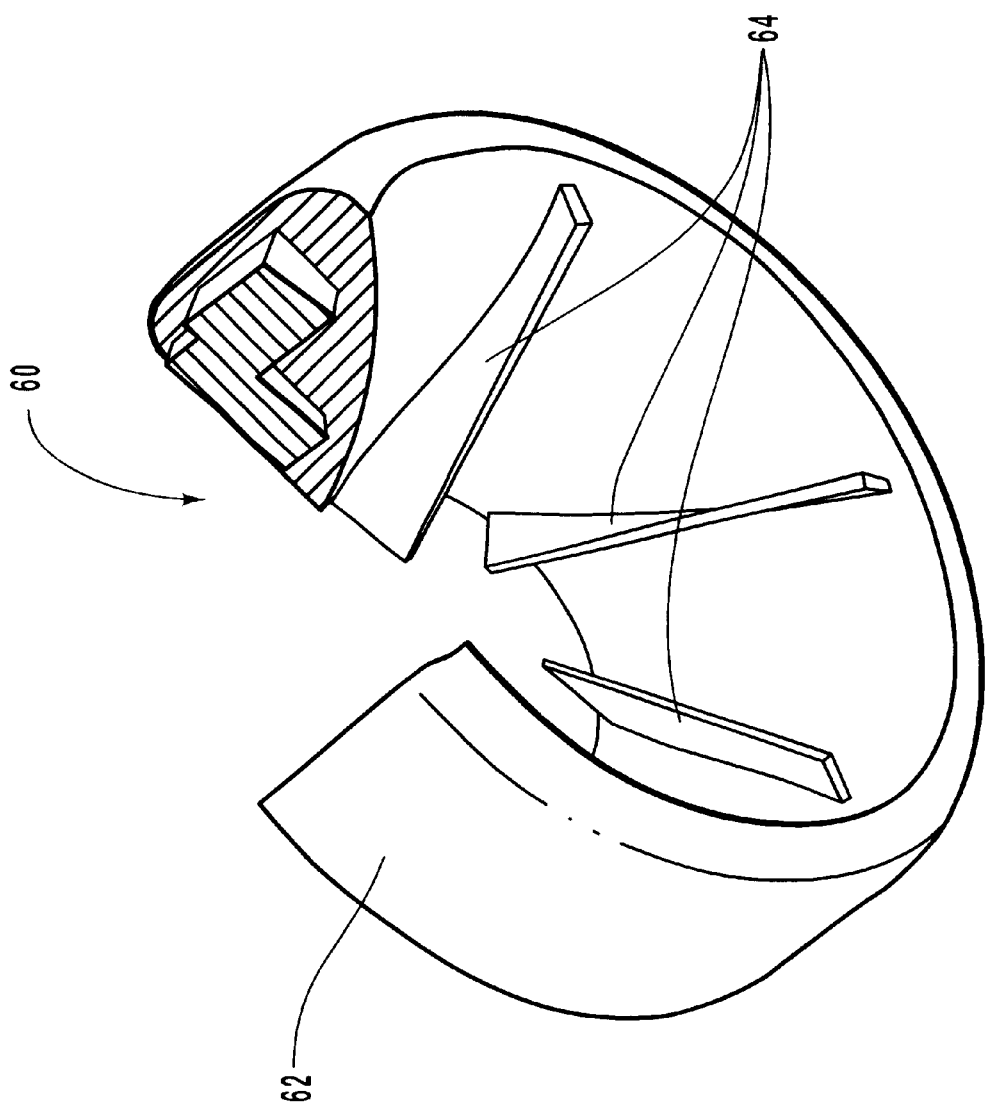
FIG. 6 is a partial isometric view illustrating an alternative rotor for the blood pump of FIG. 1.

As shown in FIG. 6, an alternative impeller assembly 60 includes a hub 62 and vanes 64. The vanes 64 extend radially inward toward the rotational axis of the impeller assembly 60.

Figure 7A:
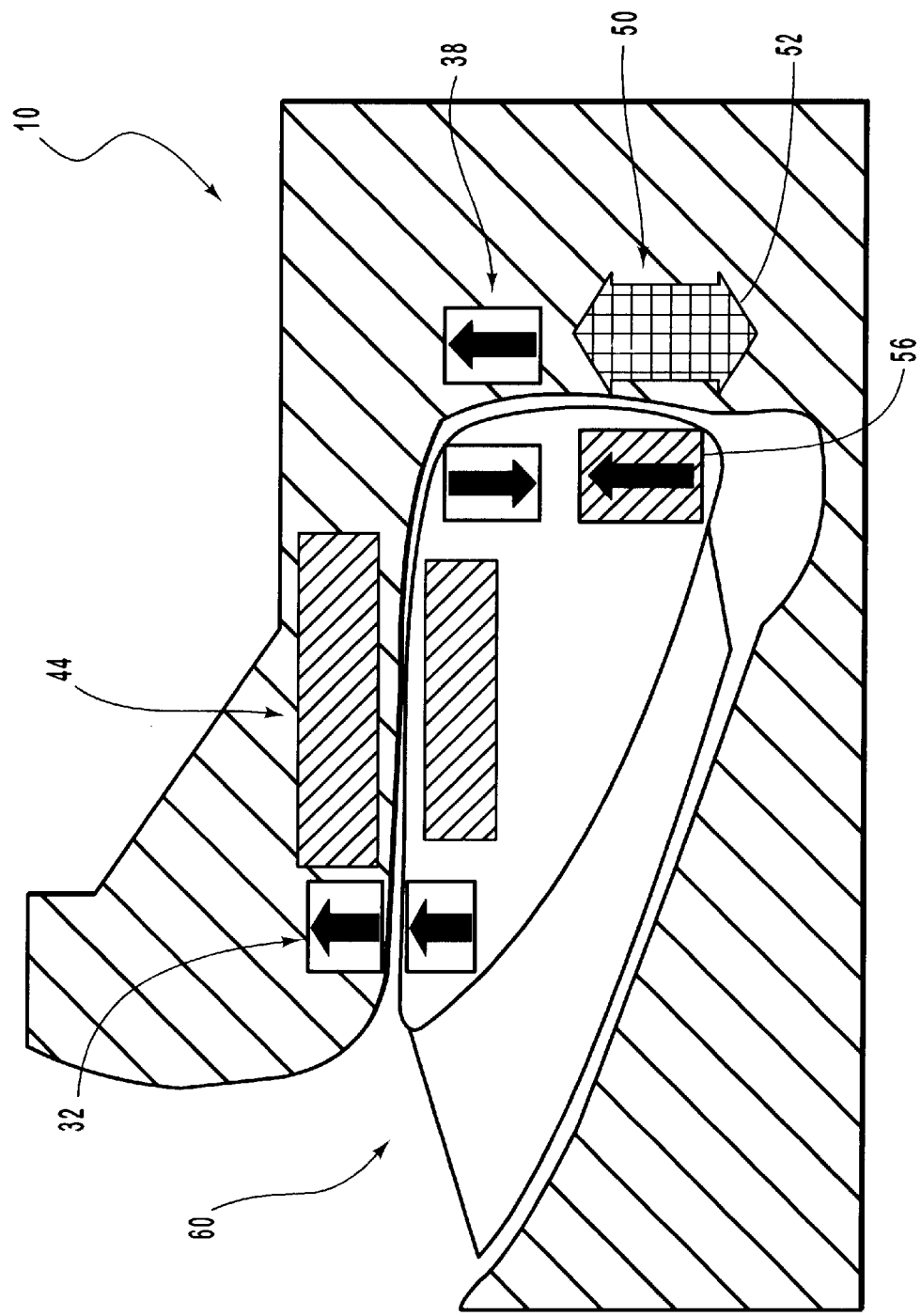
FIGS. 7A and 7B are cross-sectional, partial views illustrating alternative versions of an embodiment of a magnetic suspension and rotation assembly for the alternative rotor of FIG. 6 as incorporated into the blood pump of FIG. 1.
Figure 7B:
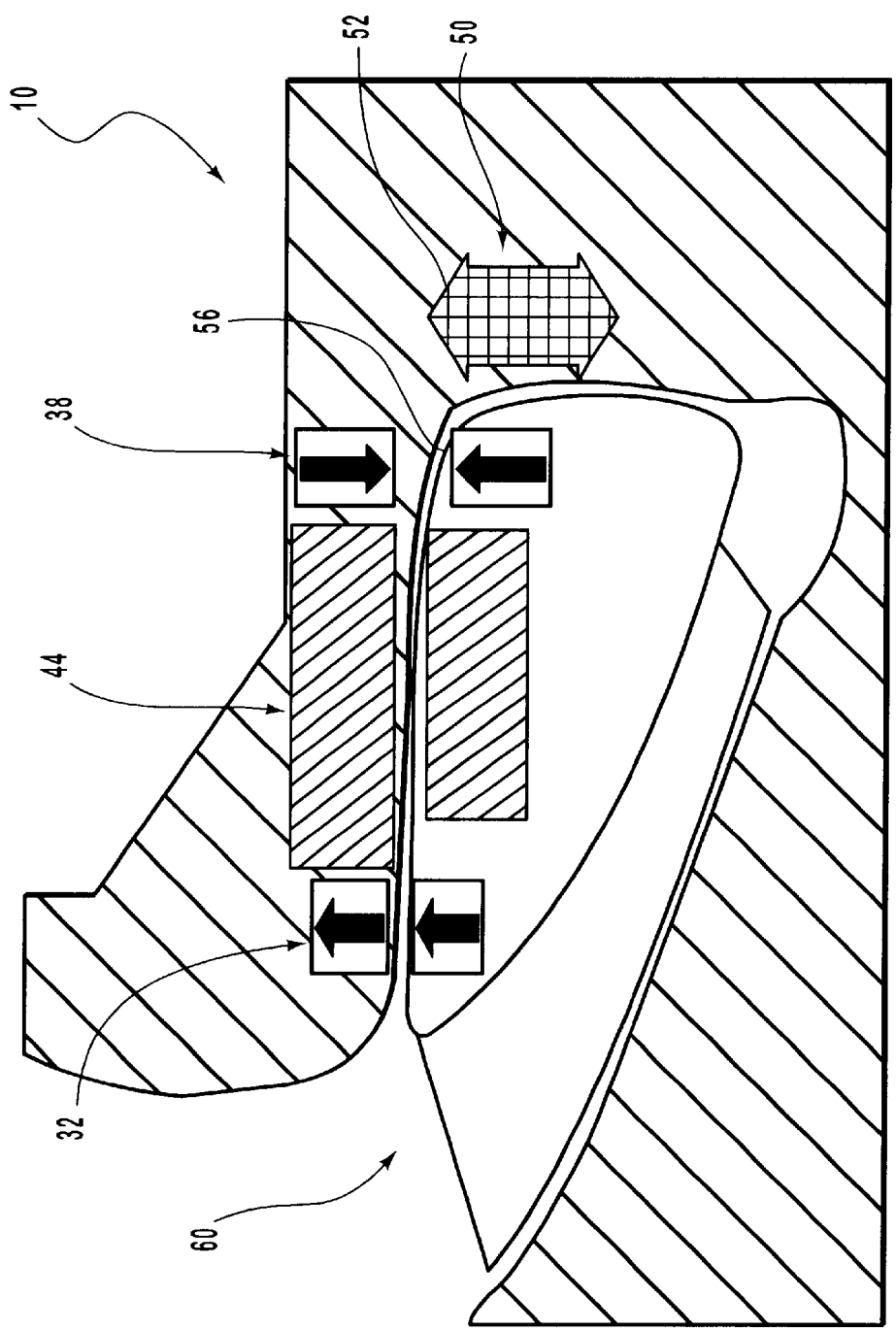

As shown in FIGS. 7A and 7B, in another alternative version of the blood pump 10 that incorporates the impeller assembly 60 of FIG. 6, the passive radial bearing 32 is repositioned at the top of the pump 10, the passive moment bearing 38 is repositioned toward the edge of the pump 10, the electromagnetic motor 44 takes up a portion of the top of the pump 10, and the electromagnetic axial bearing 50 consists of the active thrust coil 52 and the permanent magnet structure 56. In the embodiment illustrated in FIG. 7B, the axial bearing 50 and the moment bearing 38 share use of the magnet structure 56.

Figure 8:
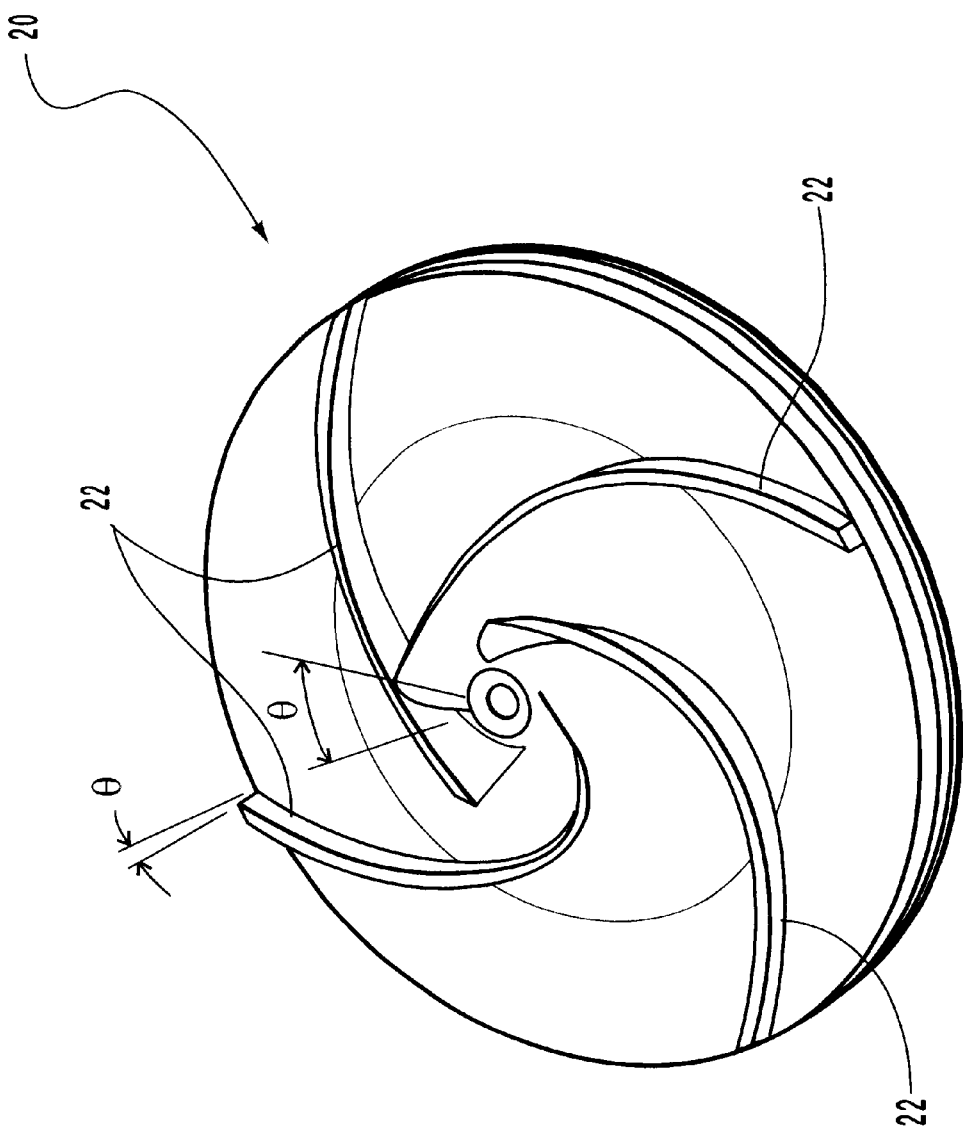
FIG. 8 is an isometric view illustrating the rotor of FIG. 2.

As shown in FIG. 8, the impeller assembly 20 includes the plurality of arcuate vanes 22. The layout of the impeller vanes 22 is designed to provide a smooth transition from the inlet blade angle to the discharge blade angle.

The pump 10 (see previous Figures) intentionally allows relatively high leakage flows along the sides of the impeller assembly 20. Relatively large fluid gaps are desirable on both sides of the impeller assembly 20 to allow for recirculating flows at low shear stress levels. As will be appreciated, the acceptable level of shear is a function of expected cell transit time. However, for both magnetic bearing and motor design considerations, it is desirable to minimize the size of a flux gap between the magnetic elements present on the impeller assembly 20 and those present in the housing 12.

Figure 9C:
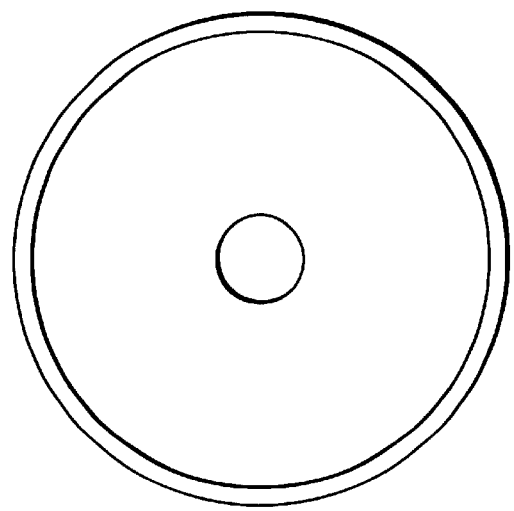
FIGS. 9A, 9B, and 9C are respective front, cross-sectional, and back views of portions of the blood pump of FIG. 1.
Figure 9B:
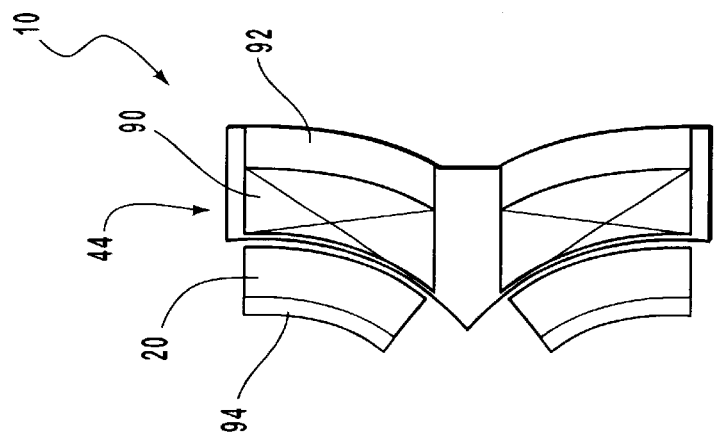
Figure 9A:
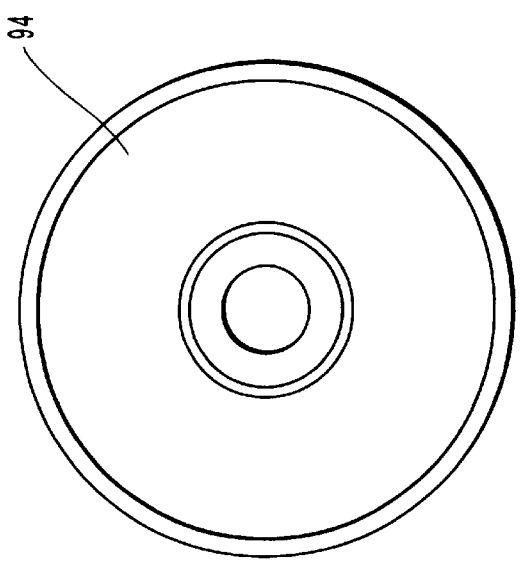

As shown in FIGS. 9A, 9B, and 9C, a portion of the pump 10 includes the impeller assembly 20 and the electromagnetic motor 44, which includes motor coils 90 having a nonmagnetic core, backed by a backing material 92, preferably a soft iron magnetic material which may or may not be laminated. Alternatively, the backing material 92 may be formed of a non-magnetic material. The impeller assembly 20 includes a ring of permanent magnets (not shown), preferably backed by a soft iron backing material 94, which acts as a magnetic yoke for the permanent magnets. The soft iron backing 94 may improve performance, but is not required.

Figure 10C:
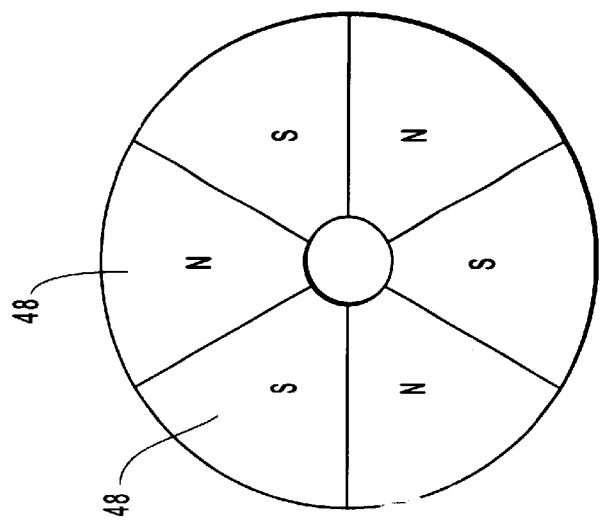
FIGS. 10A, 10B, and 10C are respective front, cross-sectional, and back views of portions of the blood pump of FIG. 1.
Figure 10B:
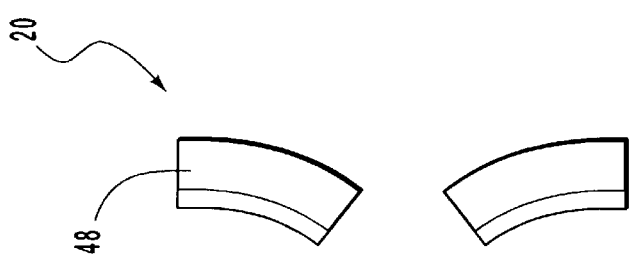
Figure 10A:
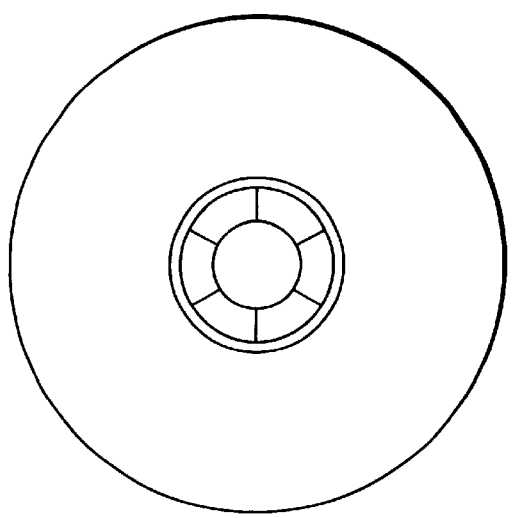

As shown in FIGS. 10A, 10B, and 10C, the impeller assembly 20 includes permanent magnets 48 arranged around the circumference of the impeller assembly 20 in alternating polarity configuration, shown in FIG. 10C by the common designations N and S. As will be appreciated, in order to provide magnetic flux across the flux gap, the magnetization of the permanent magnets 48 is perpendicular to the flux gap. In FIG. 10C, the flux of the permanent magnets 48 can be visualized as flowing into or out of the plane of the page.

Figure 11C:
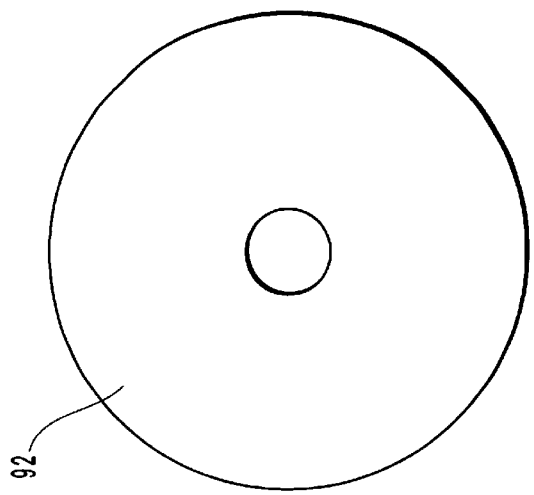
FIGS. 11A, 11B, and 11C are respective front, cross-sectional, and back views of portions of the blood pump of FIG. 1.
Figure 11B:
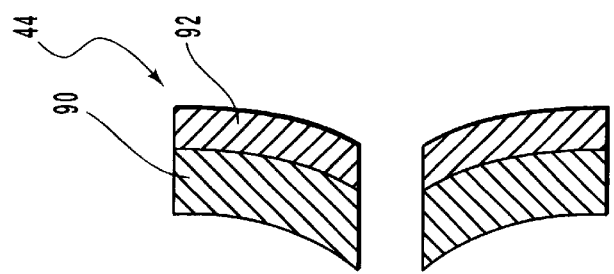
Figure 11A:
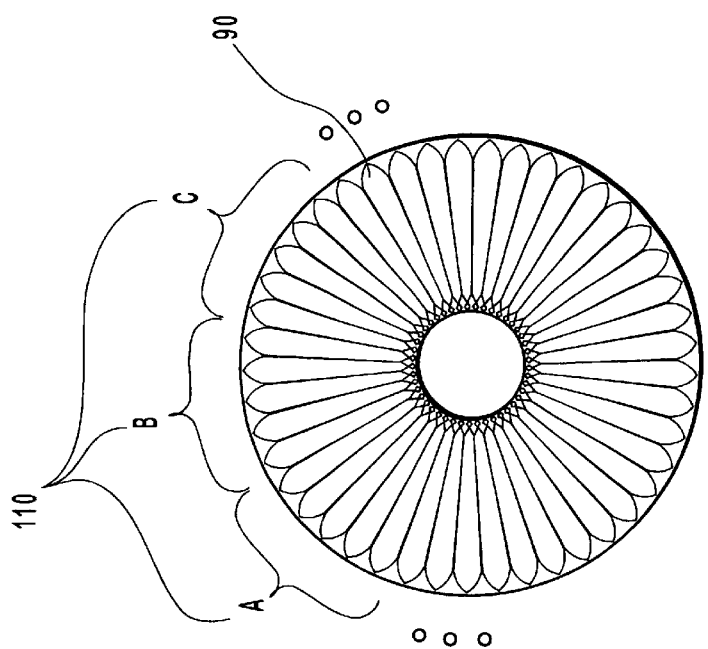

As shown in FIGS. 11A, 11B, and 11C, the electromagnetic motor 44 includes the motor coils 90 and stator soft iron backing 92. The coils 90 are separated into a plurality of discrete stator poles 110. The number of stator poles is generally divisible by the number of phases, which can be 2, 3, 4, or more. For example, in the embodiment shown, the designated stator poles (depicting one third of the stator circumference) are labeled A, B, and C because the preferred pump 10 is designed to function on 3-phase electrical power. Nine poles are thus provided, but any number that is divisible by 3 could be used with 3-phase power.

This approach to motor design has several advantages. First, the fluid/flux gap between the rotor and stator can be conformally shaped to the requirements of the fluid flow path 26 (FIG. 3A) as discussed above. Second, the motor is highly efficient due to the balance of the amount of permanent magnet material with the volume of coils and soft iron. Third, the motor can be constructed in such a way that it only generates rotational forces or generates primarily rotational forces. This is a very important advantage in a system that uses magnetic bearings, since the size and power level of the magnetic bearings depends on the magnitude of the forces other than rotational force generated by the motor. Conventional integrated pump designs for sensitive fluids do not use this approach. Additionally, this motor is a slotless motor because the coils do not comprise a magnetic core, and the magnetic material 92 is thus separated from the permanent magnets in the rotor by the dimension of the coils 90.

The support of the rotating impeller assembly 20 requires control of six degrees of freedom: three translations (x,y,z) and three rotational displacements ($M_x$, $M_y$, $M_z$). Of course, one of the rotational displacements in driven by the motor. There are several types of forces which act upon the impeller assembly 20: fluid forces, gravitational forces, and dynamic forces. The fluid forces are due to fluid pressures acting on the impeller assembly 20 and the changes in momentum as the flow direction is changed. The gravitational forces are due to the difference between the weight of the impeller and the buoyant force, in blood, acting on the impeller in different orientations, depending on the orientation of the body relative to vertical. Dynamic forces act upon the impeller due to bodily accelerations during such activities as sudden motions, impact after a fall, etc.

Blood and other fluids that are sensitive to heating are easily accommodated by this invention, because the innovative magnetic bearing design reduces power dissipated in the magnetic bearings as compared to conventional systems. This is accomplished, in part, by the use of permanent magnets. While permanent magnets have been employed in some conventional blood pumps, the embodiments in this invention present advantages in terms of 1) size of the magnetic bearing system, 2) bearing stiffness achieved in this configuration of the permanent magnets, and 3) power dissipated in the magnetic bearings.

Figure 12:
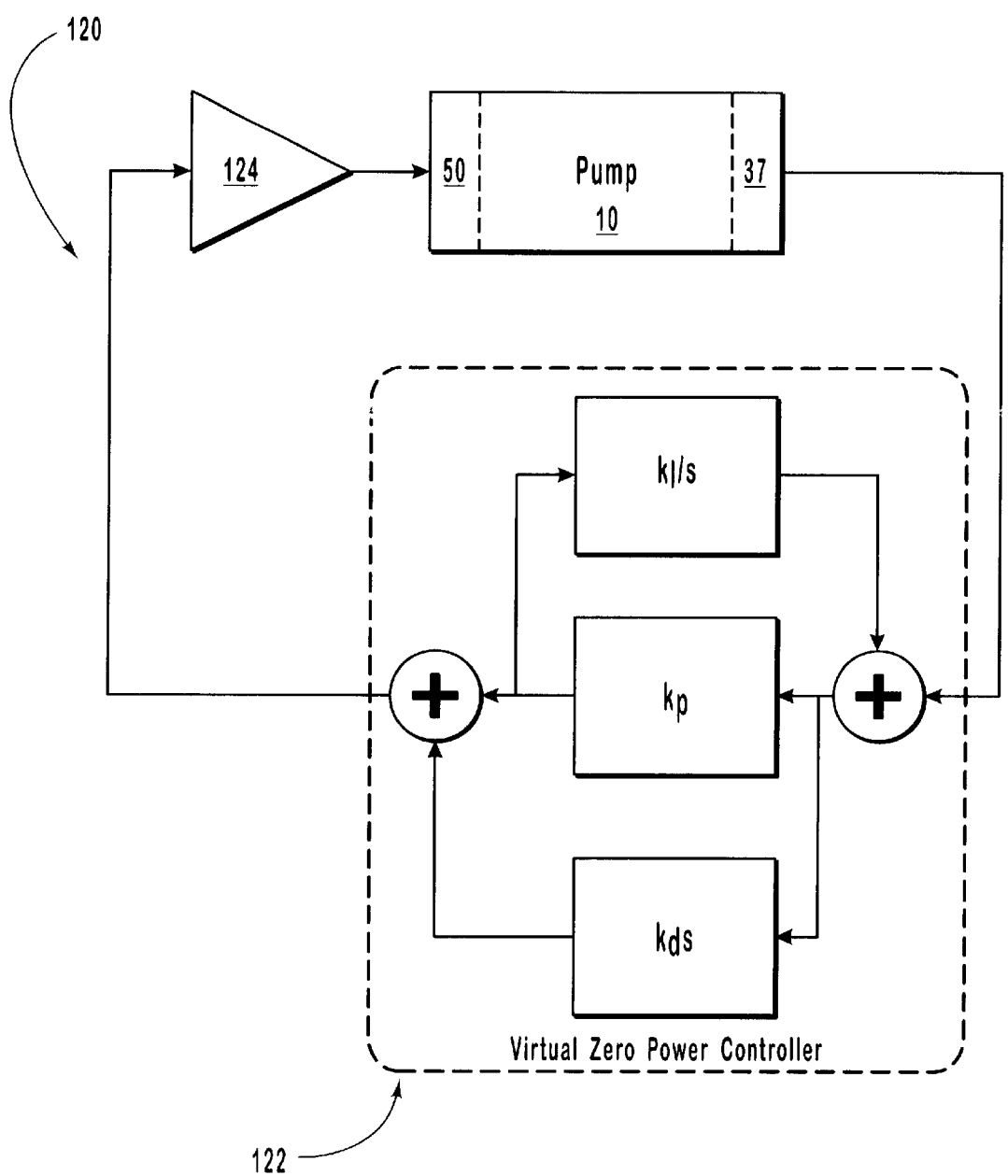
FIG. 12 is a block diagram illustrating a system including the blood pump of FIG. 1 and a Virtual Zero Power (VZP) Controller.

As shown in FIG. 12, a system 120 includes the blood pump 10 of FIG. 1 and a Virtual Zero Power (VZP) Controller 122 for controlling, the position of the impeller assembly 20 (see FIG. 3A) at an equilibrium point of the passive bearings subjected to fluid and gravitational forces. The VZP Controller 122 receives the axial position of the impeller assembly 20 from the sensor 37, and outputs an appropriate signal to a current amplifier 124 driving the axial bearing 50. As is well know in the art, the VZP Controller 122 stabilizes the impeller assembly 20 within the housing 12 and has low or zero gain at DC.

Although this invention has been described with reference to particular embodiments, the invention is not limited to these described embodiments. Rather, the invention is limited only by the appended claims, which include within their scope all equivalent devices and methods that operate according to the principles of the invention as described.

What is claimed is:

1. A blood pump comprising:

a housing having inlet and outlet ports for respectively receiving and discharging blood;

a rotor positioned in the housing's interior for pumping blood between the housing's inlet and outlet ports, the rotor operatively moving with respect to three translational and three rotational axes; and an assembly for magnetically suspending and rotating the rotor in a contact-free manner with respect to the housing, the assembly including:

only one electromagnetic bearing wherein said electromagnetic bearing actively controls the motion of the rotor with respect to one axis selected form the rotor's three translational and three rotational axes;

an electromagnetic motor wherein said electromagnetic motor actively drives the rotor with respect to one of its three rotational axis; and a plurality of magnetic bearings wherein said plurality of magnetic bearings passively controls the motion of the rotor with respect to the remaining four translational and rotational axes.

2. The blood pump of claim 1, wherein the rotor includes vanes, wherein the vanes are shrouded on only one side.

3. The blood pump of claim 1, wherein the rotor's three translational axes are coincident with the rotor's three rotational axes, wherein the electromagnetic bearing actively controls translational motion of the rotor along the translational axis coincident with the rotational axis about which the electromagnetic motor drives the rotor.

4. The blood pump of claim 1, wherein each of the magnetic bearings includes one or more magnet rings.

5. The blood pump of claim 1, wherein the electromagnetic bearing includes one or more current coils and one or more magnet rings.

6. The blood pump of claim 1, wherein the electromagnetic bearing includes one or more active thrust coils positioned in the housing and one or more permanent magnets positioned in the rotor.

7. The blood pump of claim 6, wherein the permanent magnets are shared with one of the magnetic bearings.

8. The blood pump of claim 1, wherein the electromagnetic bearing is an axial bearing.

9. The blood pump of claim 1, wherein the electromagnetic bearing is positioned at the periphery of the rotor.

10. The blood pump of claim 1, wherein the rotor includes vanes, wherein the electromagnetic motor is positioned opposite the vanes.

11. The blood pump of claim 1, wherein the rotor includes vanes, wherein the electromagnetic motor is positioned with its flux gap extending across the vanes.

12. The blood pump of claim 1, wherein the magnetic bearings include radial and moment bearings.

13. The blood pump of claim 12, wherein the rotor includes vanes, wherein the radial and moment bearings are positioned opposite the vanes.

14. The blood pump of claim 12, wherein the rotor includes vanes, wherein the radial bearings are positioned at an inner periphery of the rotor, and the moment bearings are positioned at an outer periphery of the rotor.

15. The blood pump of claim 1, wherein the magnetic bearings include permanent magnets and soft iron magnetic materials.

16. The blood pump of claim 1, further comprising a virtual zero power controller coupled to the electromagnetic bearing and the electromagnetic motor for controlling the bearing and motor such that the rotor is maintained in a null point position within a magnetic suspension field.

17. The blood pump of claim 1, wherein the rotor includes a circumferential hub and a plurality of vanes, each having a fixed end attached to an inner surface of the hub and each extending inward toward a rotational axis of the hub.

18. In a blood pump having a housing, a rotor operatively moving with a translational and rotational motion relative to the housing, a magnetic motor for driving rotational motion of the rotor relative to the housing, and a plurality of magnetic bearings for passively controlling translational and rotational motion of the rotor, an apparatus for stabilizing suspension and rotation of the rotor in a contact-free manner with respect to the housing, the apparatus consisting essentially of:
    an electromagnetic bearing structure wherein said electromagnetic bearing structure actively controls only one axis of motion of the rotor relative to the housing.

19. The apparatus of claim 18, wherein the electromagnetic bearing structure comprises an axial bearing including an active thrust coil and a permanent magnet.

20. An artificial heart comprising:
a left ventricular blood pump comprising:
a first housing having inlet and outlet ports for respectively receiving and discharging blood;
a first rotor positioned in the first housing's interior for pumping blood between the first housing's inlet and outlet ports, the first rotor operatively moving with respect to three translational and three rotational axes; and
a first assembly for magnetically suspending and rotating the first rotor in a contact-free manner with respect to the first housing, the first assembly including:
only one first electromagnetic bearing wherein said electromagnetic bearing actively controls the motion of the first rotor with respect to one axis selected form the first rotor's three translational and three rotational axes;
a first electromagnetic motor wherein said electromagnetic motor actively drives the first rotor with respect to one of its three rotational axis; and
a first plurality of magnetic bearings wherein said plurality of magnetic bearings passively controls the motion of the first rotor with respect to four translational and rotational axes; and
a right ventricular blood pump comprising:
a second housing having inlet and outlet ports for respectively receiving and discharging blood;
a second rotor positioned in the second housing's interior for pumping blood between the second housing's inlet and outlet ports, the second rotor operatively moving with respect to three translational and three rotational axes; and
a second assembly for magnetically suspending and rotating the second rotor in a contact-free manner with respect to the second housing, the second assembly including:
only one second electromagnetic bearing wherein said electromagnetic bearing actively controls the motion of the second rotor with respect to one axis selected form the second rotor's three translational and three rotational axes;
a second electromagnetic motor wherein said electromagnetic motor actively drives the second rotor with respect to one of its three rotational axis; and
a second plurality of magnetic bearings wherein said plurality of magnetic bearings passively controls the motion of the second rotor with respect to four translational and rotational axes.

21. A method for pumping blood through an animal's body, the method comprising:
immersing a pump rotor capable of motion in three translational and three rotational axes in the blood;
magnetically suspending the pump rotor in a contact-free manner with a plurality of passive magnetic bearings and only one active electromagnetic bearing structure;
rotating the pump rotor with a magnetic motor; and
actively controlling the magnetic suspension and rotation of the pump rotor with respect to only one of the pump rotor's three translational and three rotational axes using the electromagnetic bearing structure.

* * * * *